United States Patent
Brockway et al.

(10) Patent No.: US 6,296,615 B1
(45) Date of Patent: *Oct. 2, 2001

(54) CATHETER WITH PHYSIOLOGICAL SENSOR

(75) Inventors: Brian P. Brockway, Shoreview; Lynn M. Zwiers, Lino Lakes; Perry A. Mills, Arden Hills; Mark J. Drexler, St. Paul, all of MN (US)

(73) Assignee: Data Sciences International, Inc., St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/264,147

(22) Filed: Mar. 5, 1999

(51) Int. Cl.[7] ................................................ A61B 5/02
(52) U.S. Cl. ............................ 600/486; 600/485; 604/27
(58) Field of Search .................... 600/486, 485, 600/466, 467, 468, 433, 434, 435; 604/27, 28

(56) References Cited

U.S. PATENT DOCUMENTS

| Re. 30,366 | 8/1980 | Rasor et al. ................... 128/419 P |
| 3,942,382 | 3/1976 | Hok ................................. 73/398 |
| 4,207,903 | 6/1980 | O'Neill ........................... 128/785 |
| 4,494,950 | 1/1985 | Fischell .......................... 604/66 |

(List continued on next page.)

FOREIGN PATENT DOCUMENTS

| 19644856 | 5/1997 | (DE) . |
| 0337035 | 10/1989 | (EP) ............................ 607/127 |
| 0482487 | 4/1992 | (EP) . |
| 95/33517 | 6/1995 | (WO) ...................... A61N/1/365 |
| 97/09926 | 3/1997 | (WO) .......................... A61B/5/02 |
| 97/33513 | 3/1997 | (WO) .......................... A61B/5/00 |
| 97/32518 | 9/1997 | (WO) ........................ A61B/5/0215 |
| WO97/32518 | 9/1997 | (WO) . |
| WO97/32519 | 9/1997 | (WO) . |

OTHER PUBLICATIONS

"Medtronic Announces Two Major Milestones in its Effort to Treat Patients with Heart Failure", *Medtronic Press Release* (2 pages), (Aug. 18, 1998).

(List continued on next page.)

*Primary Examiner*—Cary O'Connor
*Assistant Examiner*—Navin Natnithithadha
(74) *Attorney, Agent, or Firm*—Schwegman, Lundberg, Woessner & Kluth, P.A.

(57) ABSTRACT

The disclosed embodiments present improved catheters with physiological sensors. In one embodiment, the catheter includes, generally, a pressure transducer/electronics assembly connected to a pressure transmission catheter. The pressure transmission catheter includes a hollow tube made from a low compliance material. The distal end of the hollow tube is filled with a gel-like material or plug which acts as a barrier between the catheter liquid and the target fluid. The hollow tube is partially filled with a low viscosity liquid and is in fluid communication with the gel-like material and the pressure transducer. The pressure of the target fluid is transmitted to the liquid in the hollow tube through the gel-like material and/or the wall of the distal tip and is fluidically transmitted to the pressure transducer. The pressure transmission catheter is capable of being inserted into a vessel lumen or inserted into a lumen of a therapeutic or diagnostic catheter for biomedical applications. This provides the ability to directly measure the pressure effects of the treatment catheter. In another embodiment, the distal end of the pressure transmission catheter may be electrically conductive so as to detect and transmit an electric signal. Thus, in this embodiment, the catheter can be used to detect a physiological signal.

75 Claims, 9 Drawing Sheets

U.S. PATENT DOCUMENTS

| | | | |
|---|---|---|---|
| 4,596,563 | | 6/1986 | Pande .................................. 604/264 |
| 4,718,425 | | 1/1988 | Tanaka et al. ...................... 128/673 |
| 4,796,641 | * | 1/1989 | Mills et al. .......................... 600/561 |
| 4,846,191 | * | 7/1989 | Brockway et al. .................. 600/561 |
| 4,899,752 | | 2/1990 | Cohen .......................... 128/419 PG |
| 4,913,147 | | 4/1990 | Fahlstrom et al. ............... 128/419 P |
| 4,921,483 | * | 5/1990 | Wijay et al. ....................... 604/103.1 |
| 4,934,369 | * | 6/1990 | Maxwell ............................. 600/311 |
| 4,987,897 | | 1/1991 | Funke ........................... 128/419 PG |
| 5,129,394 | | 7/1992 | Mehra ........................... 128/419 PG |
| 5,192,314 | | 3/1993 | Daskalakis .............................. 623/3 |
| 5,199,427 | | 4/1993 | Strickland ..................... 128/207.14 |
| 5,218,957 | | 6/1993 | Strickland ..................... 128/200.26 |
| 5,348,536 | | 9/1994 | Young et al. ........................... 604/43 |
| 5,353,800 | | 10/1994 | Pohndorf et al. .................... 128/673 |
| 5,373,852 | | 12/1994 | Harrison et al. ..................... 128/733 |
| 5,431,171 | | 7/1995 | Harrison et al. ..................... 128/698 |
| 5,458,585 | * | 10/1995 | Salmon et al. ....................... 604/528 |
| 5,487,760 | | 1/1996 | Villafana ................................. 623/2 |
| 5,535,752 | | 7/1996 | Halperin et al. ..................... 128/670 |
| 5,538,005 | | 7/1996 | Harrison et al. ..................... 128/698 |
| 5,545,151 | | 8/1996 | O'Connor et al. ................... 604/282 |
| 5,551,427 | | 9/1996 | Altman ................................. 128/642 |
| 5,593,430 | | 1/1997 | Renger .................................. 607/18 |
| 5,702,427 | | 12/1997 | Ecker et al. ........................... 607/28 |
| 5,796,827 | | 8/1998 | Coppersmith et al. .................. 380/9 |
| 5,807,265 | | 9/1998 | Itoigawa et al. ..................... 600/486 |
| 5,836,886 | | 11/1998 | Itoigawa et al. ..................... 600/488 |
| 5,860,938 | | 1/1999 | Lafontaine et al. ................. 600/585 |
| 5,899,927 | | 5/1999 | Ecker et al. ........................... 607/23 |
| 6,015,386 | | 1/2000 | Kensey et al. ....................... 600/486 |
| 6,019,729 | * | 2/2000 | Itoigawa et al. ..................... 600/488 |
| 6,019,735 | * | 2/2000 | Kensey et al. ....................... 600/573 |
| 6,024,704 | | 2/2000 | Meador et al. ...................... 600/486 |
| 6,033,366 | * | 3/2000 | Brockway et al. .................. 600/486 |

OTHER PUBLICATIONS

"Respiration Monitoring System Based on Sensed Blood Pressure Variations", Copy of Application Serial No. 08/819,888 as filed on Sep. 28, 1995, 17 Pages, (copy not enclosed).

Brockway, B.P., et al., "A New Method for Continuous Chronic Measurement and Recording of Blood Pressure, Heart Rate and Activity in the Rat Via Radio–Telemetry", *Clinical and Experimental Hypertension—Theory and Practice,* A13(5), pp 885–895, (1991).

Sato, K., et al., "Evaluation of a New Method Using Telemetry for Monitoring the Left Ventricular Pressure in Free–Moving Rats", *J. Pharm. & Tox. Methods;* vol. 31, No. 4, pp. 191–198, (Aug. 1994).

van den Buuse, M., "Circadian Rhythms of Blood Pressure, Heart Rate, and Locomotor Activity in Spontaneously Hypertensive Rats as Measured with Radio–Telemetry", *Phys. & Behavior;* 55 (4), pp. 783–787, (1994).

Zimmerman, T.G., "Personal Area Networks: Near–field intrabody communication", *IBM Systems Journal* (USA), vol. 35 (3–4), pp. 609–617, (1996).

* cited by examiner

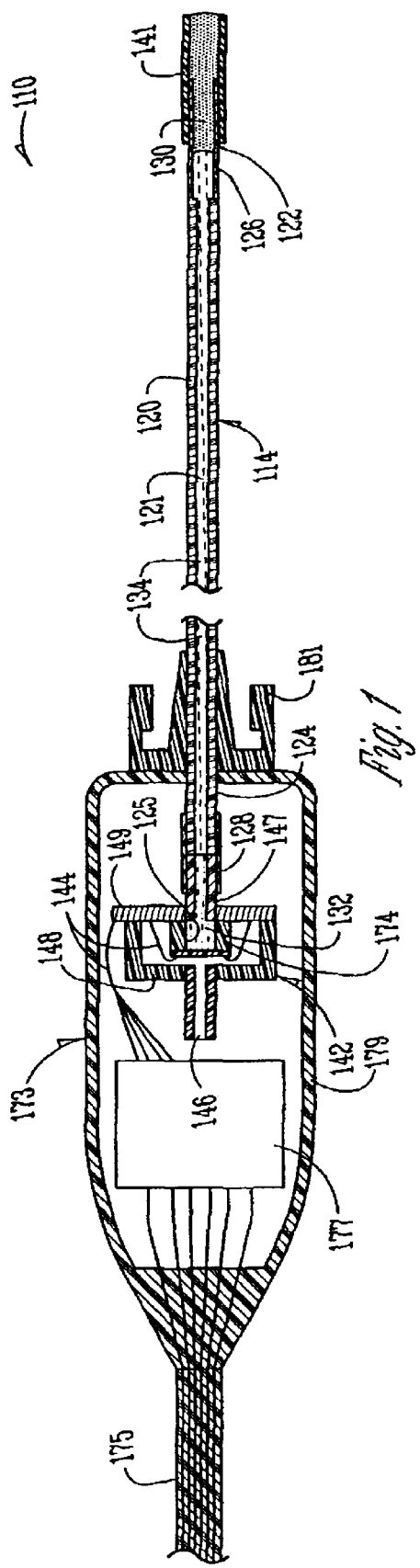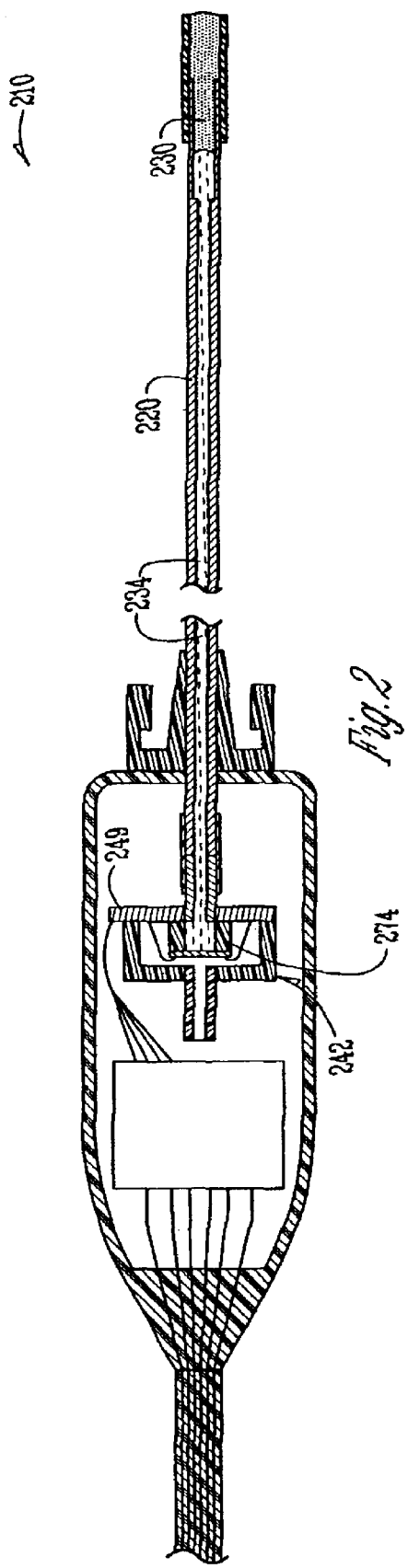

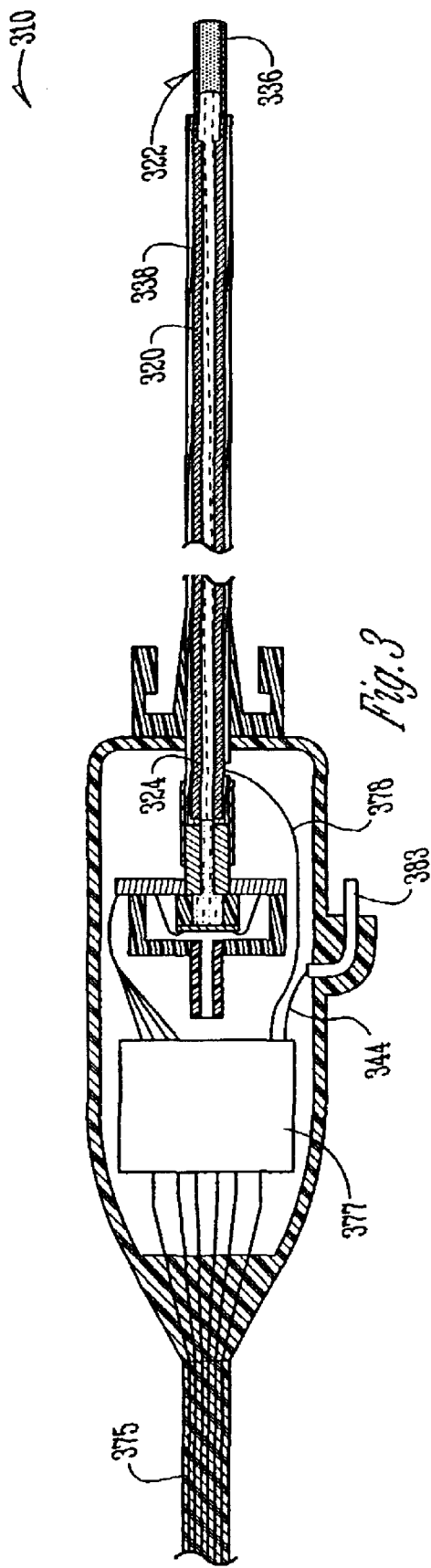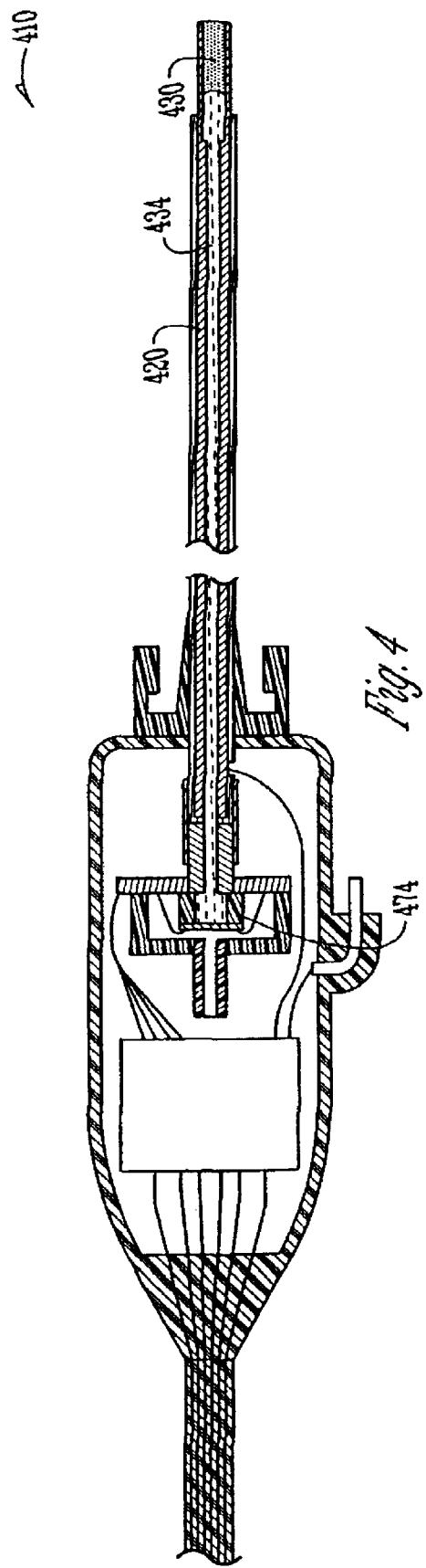

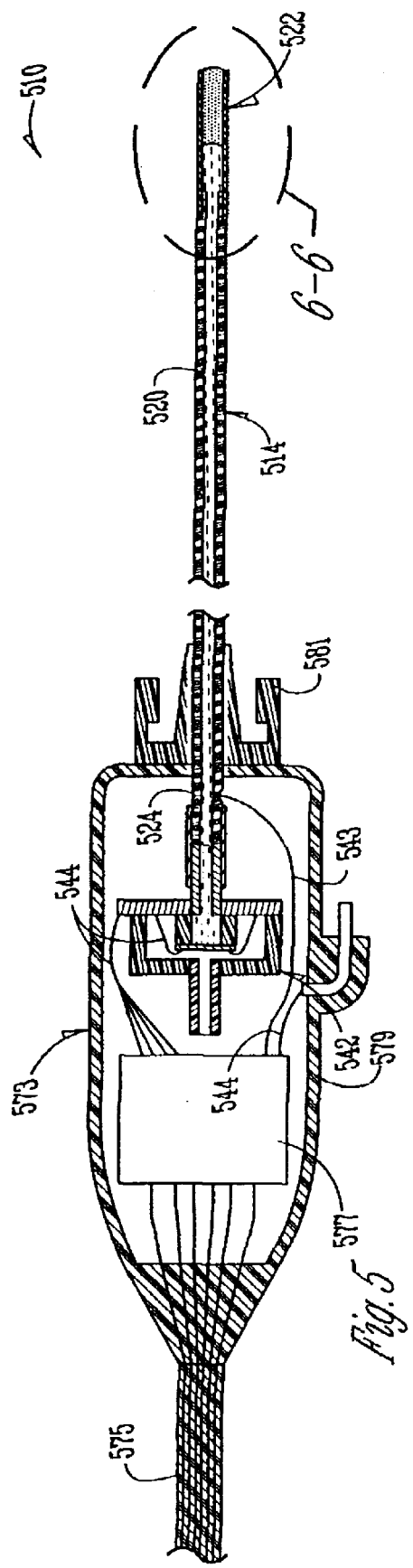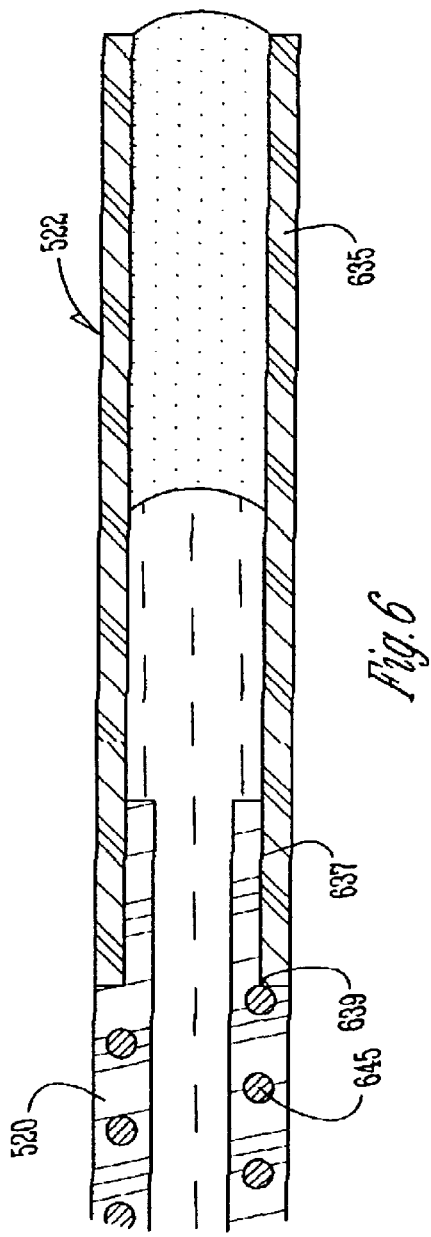

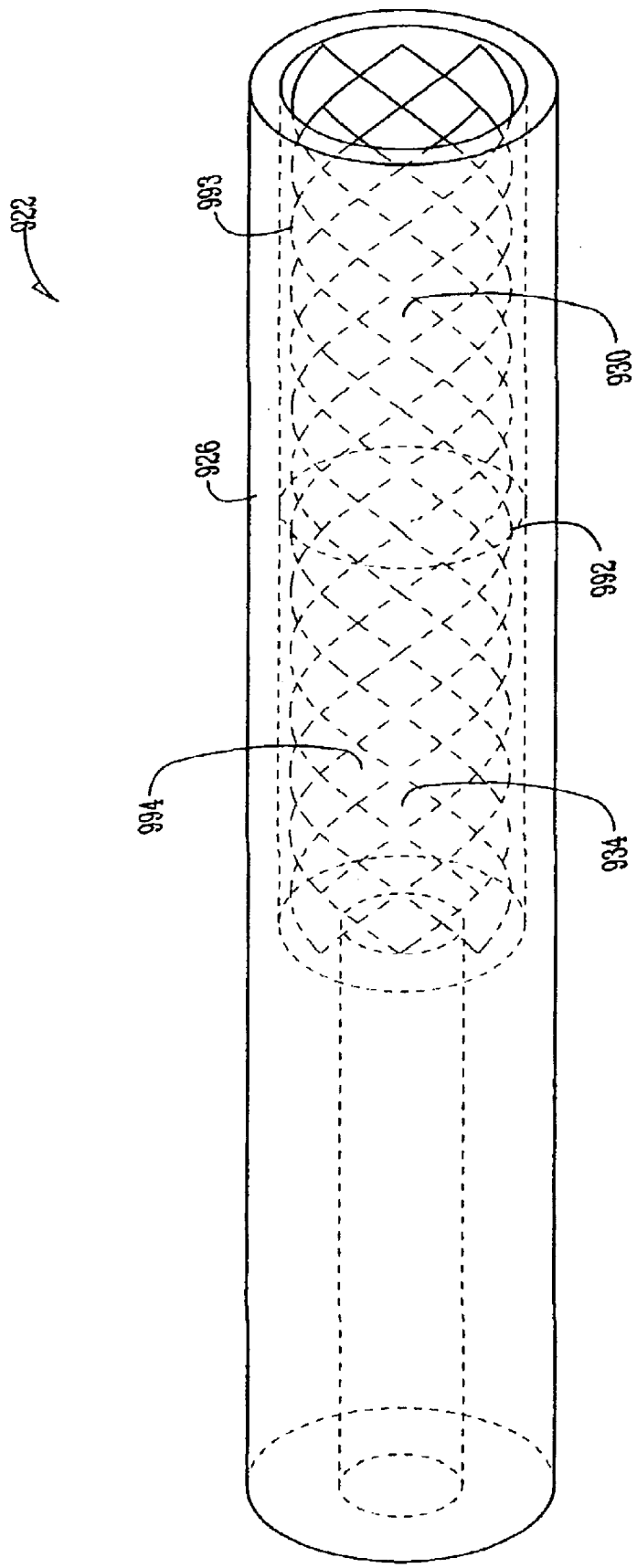

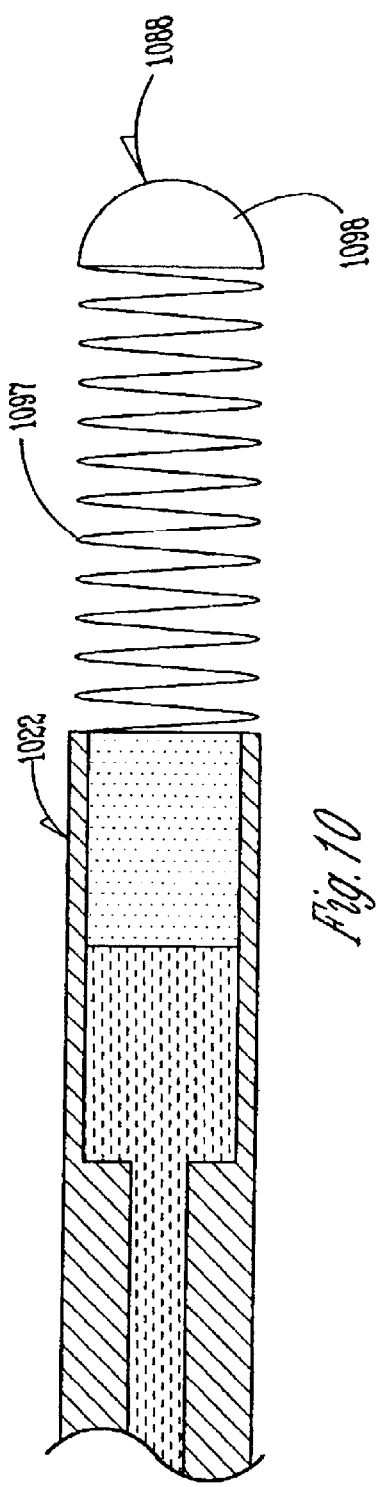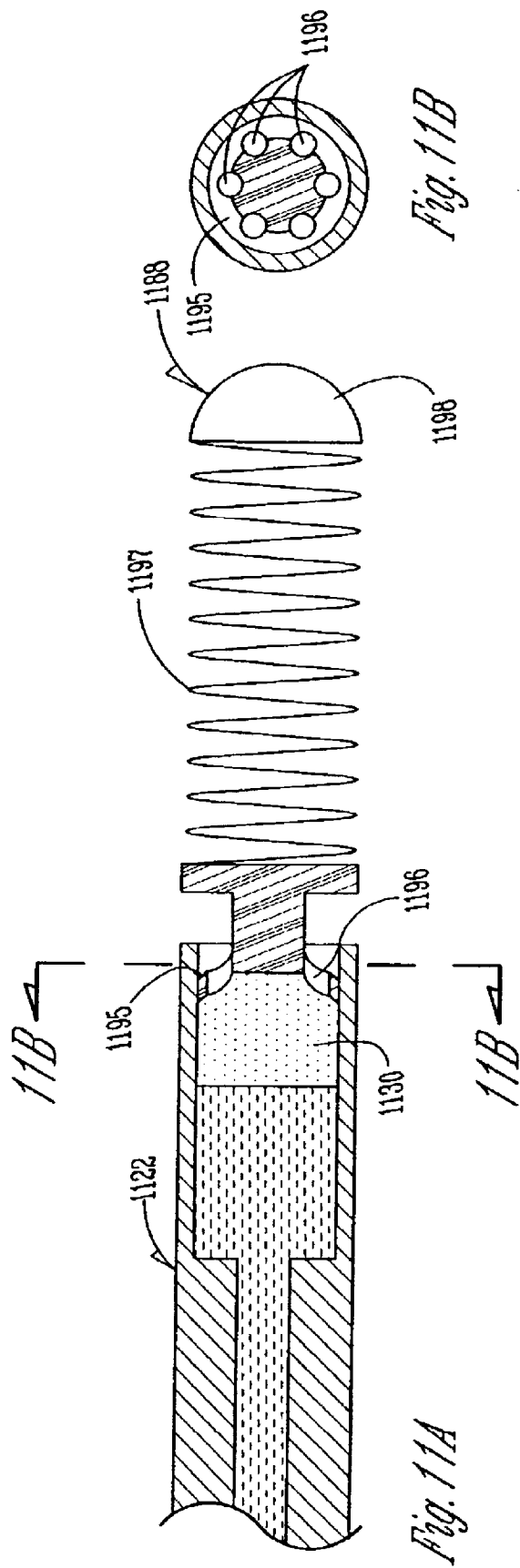

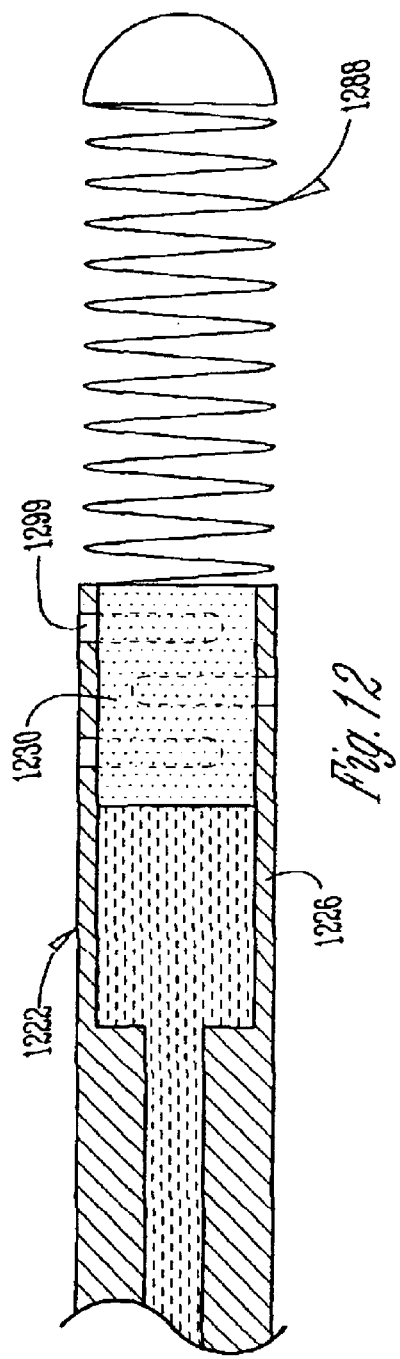
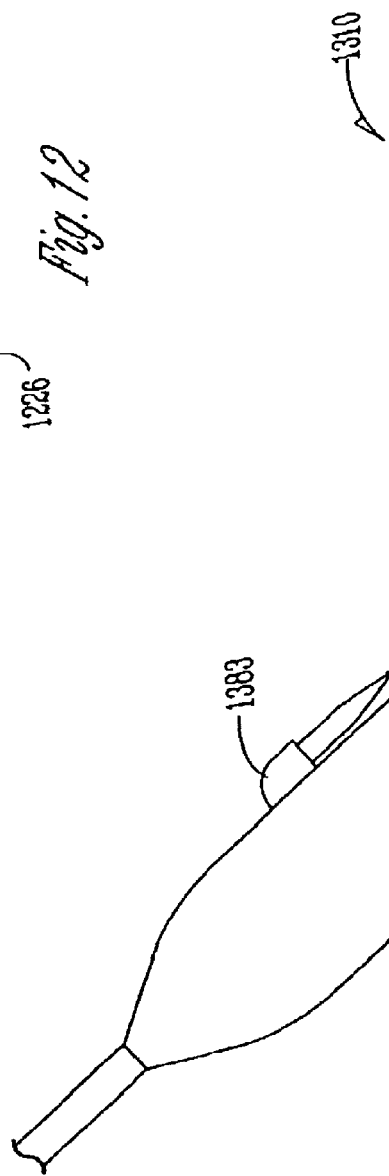

CATHETER WITH PHYSIOLOGICAL SENSOR

RELATED APPLICATION

The present invention is related to U.S. patent application No. 09/159,653, filed Sept. 24, 1998, title "IMPLANTABLE SENSOR WITH WIRELESS COMMUNICATION"

TECHNICAL FIELD

The described embodiments generally relate to catheters, and more particularly, to catheters capable of sensing physiological pressures, such as blood pressure, intracranial pressure, intrapleural pressure, bladder pressure, and pressure within the gastro-intestinal system, and of sensing an electric signal, such as an electrocardiogram.

BACKGROUND

U.S. Pat. No. 4,846,191, of Brian P. Brockway et al. (hereinafter the Brockway et al. '191 patent) discloses a pressure measurement device for sensing physiological pressures. The device consists generally of a pressure transducer with associated electronics and a pressure transmission catheter. The distal tip of the catheter senses the pressure of the target site and transmits the pressure fluidically through the catheter to be sensed by the pressure transducer.

In one embodiment of the Brockway et al. '191 patent, the pressure transmission catheter consists of a small diameter hollow tube which is filled with a low viscosity liquid. This liquid is in fluid communication with the pressure transducer at the proximal end of the hollow tube and a gel-like material at the distal end. The gel-like material provides a direct interface with the tissue or body fluid of which the pressure is to be measured.

Pressure measurement catheters such as described in the Brockway et al. '191 patent have been used to augment/support therapeutic treatments, as well as provide valuable information for diagnosis. For example, blood pressure measurements are very important when percutaneous therapeutic catheters affect blood pressure. Examples of therapeutic catheters include intra-aortic balloon catheters, angioplasty catheters, and perfusion catheters.

Taking one type of therapeutic catheter as an example, intra-aortic balloon catheters are designed to assist a failing heart through cyclic inflation-deflation of a balloon placed in the descending thoracic aorta, in counterpulsation to the heart. In a typical procedure, a guidewire (a thin flexible wire) is inserted through an incision into the common femoral artery and is directed through the delicate, tortuous and narrow vasculature. Once the guidewire is positioned, the intra-aortic balloon catheter is passed over the guidewire, utilizing the guidewire lumen of the catheter, until the balloon reaches the desired location.

The balloon is connected through a series of thin tubes to a control system which controls the balloon's inflation and deflation, repeatedly, in synchrony with a patient's heart beat. The action of the balloon assumes some of the load of the heart mainly by increasing systolic pressure which increases the flow of blood through the coronary arteries. In order to synchronize the balloon inflation/deflation with the heart beat, the patient's heart electric signal or electrocardiogram is detected using surface electrodes attached to the skin of the patient. These electrodes are connected to the control system of the intra-aortic balloon catheter. Inflation of the balloon occurs at a specified time relative to a reference signal on the patient's electrocardiogram.

The intra-aortic balloon catheter system of the Brockway et al. '191 patent, as described above, has its limitations. For example, the surface electrodes used to detect the patient's electrocardiogram for balloon inflation/deflation control have a limitation in that the signal can be relatively weak and noisy, leading potentially to spurious or unreliable responses. Further, the electrodes may become disengaged from the patient's skin due to lack of adhesion or being knocked off. Additionally, the patient typically has one set of surface electrodes attached for general monitoring; adding a second set of electrodes for controlling the intra-aortic balloon catheter adds further complexity and discomfort for the patient.

Blood pressure is typically used to calibrate the intra-aortic balloon catheter system. Ideally, this pressure should be measured in the vicinity of the catheter balloon. The electric signals sensed by the electrodes are used as the primary trigger for the catheter control system to pneumatically inflate the balloon, and the pressure signals are used to temporally calibrate balloon inflation to the electrical signals.

In the treatment modality of the Brockway et al. '191 patent, once the therapeutic catheter is placed, the guidewire is removed from the catheter's guidewire lumen. The guidewire lumen is then flushed with saline, or saline with anticoagulation agents such as heparin, in order to "fill" the guidewire lumen with a liquid. Once filled, the proximal end of the catheter is connected to a pressure transducer. In this respect, blood pressure upstream of the balloon is fluidically transmitted through the saline and detected by the pressure transducer.

This approach has its limitations for accurately measuring the pressure, especially with smaller balloon catheters having small guidewire lumens. Limitations may include high system compliance, the presence of air bubbles in the guidewire lumen, and possible blood coagulation in the guidewire lumen. Compliance is a property of this measurement system that provides a measure of resistance to deformation due to pressure. A system with high compliance will deform more than a low compliance system as pressure is increased. A high compliance system will tend to absorb rapid pressure changes that should be transmitted through the liquid in the lumen. This, in tun, reduces the accuracy of the pressure measurements as a result of lowering the frequency response. Excessive air bubbles and thrombus in the guidewire lumen can also result in dampening and loss of accuracy of the measured blood pressure signal. This can reduce the efficacy of the inflation of the balloon.

A further limitation of the system of the Brockway et al. '191 patent is that it is labor intensive. There is the additional preparation required by the user to fill the guidewire lumen just prior to use. Improper filling may lead to bubble formation in the catheter lumen. It is also necessary to flush the lumen to remove thrombus that may form, otherwise the pressure signal might be blocked altogether.

What is needed is an improved apparatus to obtain more reliable and higher quality measurements of blood pressure. An improved apparatus for sensing an electric signal is also needed.

SUMMARY

The disclosed embodiments present improved catheters with physiological sensors. In one embodiment, the catheter includes, generally, a pressure transducer/electronics assembly connected to a pressure transmission catheter. The pressure transmission catheter includes a hollow tube made from a low compliance material. The distal end of the hollow tube is filled with a gel-like material or plug which acts as a barrier between the catheter liquid and the target fluid. The hollow tube is partially filled with a low viscosity liquid and is in fluid communication with the gel-like material and the pressure transducer. The pressure of the target fluid is transmitted to the liquid in the hollow tube through the gel-like material and/or the wall of the distal tip and is fluidically transmitted to the pressure transducer. The pressure transmission catheter is capable of being used by itself or it can be inserted into a lumen of a therapeutic or diagnostic catheter for biomedical applications. This provides the ability to directly measure the pressure effects of the treatment catheter.

In another embodiment, the distal end of the pressure transmission catheter may be electrically conductive so as to detect and transmit electrical signals. Thus, in this embodiment, the catheter can be used to detect a physiological parameter manifested as an electrical current.

BRIEF DESCRIPTION OF THE DRAWINGS

FIG. 1 is a partial cross-sectional side view of an embodiment of a pressure sensing catheter.

FIG. 2 is a partial cross-sectional side view of an embodiment of a pressure sensing catheter.

FIG. 3 is a partial cross-sectional side view of an embodiment of a pressure and electric signal sensing catheter.

FIG. 4 is a partial cross-sectional side view of an embodiment of a pressure and electric signal sensing catheter.

FIG. 5 is a partial cross-sectional side view of an embodiment of a pressure and electric signal sensing catheter.

FIG. 6 is a cross-sectional side view of an embodiment of a distal end of the pressure and electric signal sensing catheter of FIG. 5.

FIG. 9 is a partial cross-sectional side view of an embodiment of a distal end of a catheter with a physiological sensor.

FIG. 10 is a partial cross-sectional side view of an embodiment of a distal end of a catheter with a physiological sensor.

FIG. 11A is a partial cross-sectional side view of an embodiment of a distal end of a catheter with a physiological sensor.

FIG. 11B is a cross-sectional view at line 11B of the distal end of the embodiment of a catheter with a physiological sensor of FIG. 11A.

FIG. 12 is a partial cross-sectional side view of an embodiment of a distal end of a catheter with a physiological sensor.

FIG. 13 is a side view, partly in section, of an embodiment of a pressure and electric signal sensing catheter inserted within a lumen of a therapeutic catheter.

DETAILED DESCRIPTION

Figure 7:
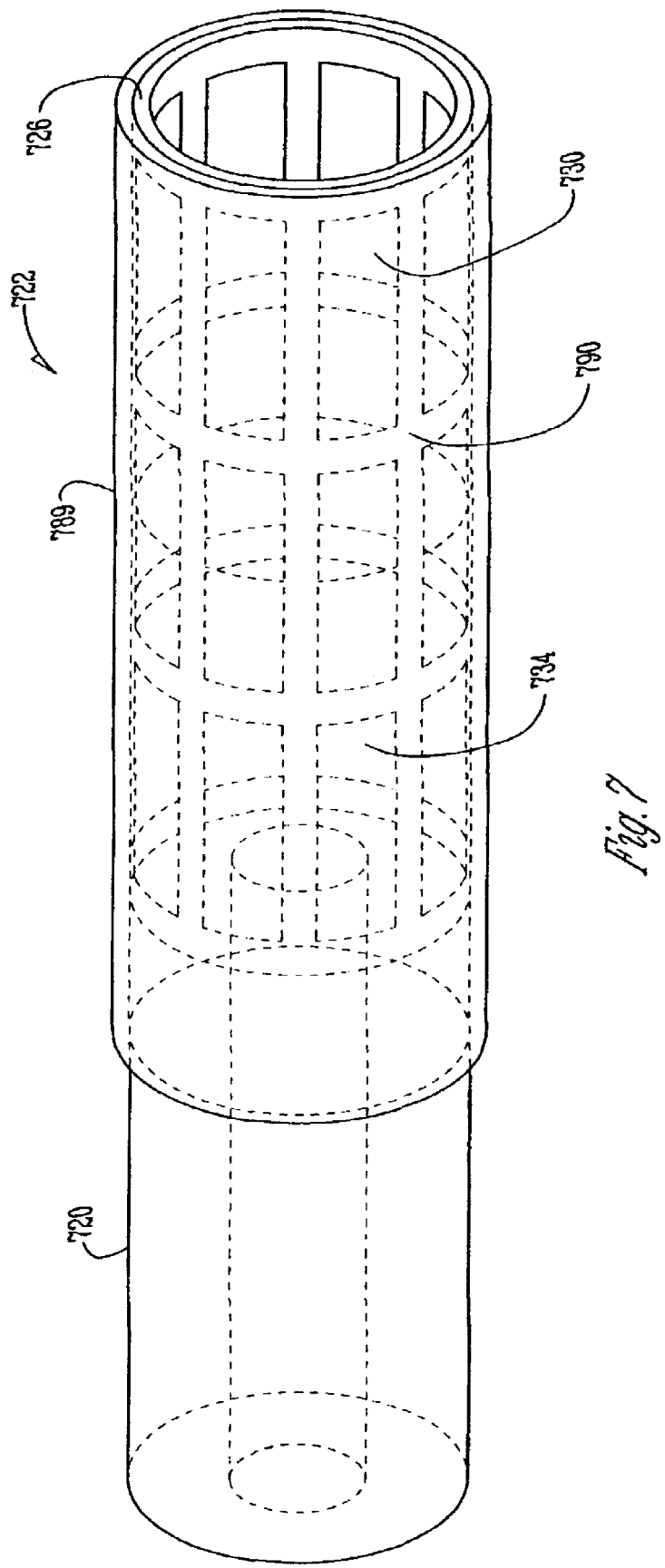
FIG. 7 is a partial cross-sectional side view of an embodiment of a distal end of a catheter with a physiological sensor.

In the following detailed description, reference is made to the accompanying drawings, which are not necessarily to scale, which form a part hereof, and in which is shown by way of illustrating specific embodiments in which the device may be practiced. These embodiments are described in sufficient detail to enable those skilled in the art to practice the device, and it is to be understood that the embodiments may be combined, or that other embodiments may be utilized and that structural and electrical changes may be made without departing from the spirit and scope. The following detailed description is, therefore, not to be taken in a limiting sense, and the scope is defined by the appended claims and their equivalents. In the drawings, like numerals describe substantially similar components throughout the several views.

The present apparatus and methods will be described in applications involving biomedical applications. However, it is understood that the present apparatus and methods may be employed in other environments and uses.

One embodiment presents a pressure sensing catheter that can be inserted into and through a lumen of therapeutic/diagnostic catheters. FIG. 1 is a partial cross-sectional side view illustrating generally, by way of example, but not by way of limitation, one embodiment of portions of a pressure sensing catheter 110. Pressure sensing catheter 110 comprises, generally, a pressure transducer/electronics assembly 173 and a pressure transmitting catheter 114.

Pressure transducer/electronics assembly 173 comprises a main housing 179 which contains transducer 142, sensor electrical connections 144, temperature compensation electronics 177, connected to cable 175. Transducer 142 comprises a housing 148, a pressure sensor 174, and an opening 146. Sensor 174 comprises, for example, a silicon diaphragm sensor or other appropriate sensor. Opening 146 provides for a gauge reference pressure. Gauge reference pressure (atmospheric pressure) is used for comparison to the measured pressure. Electronics 177 comprise temperature compensation circuitry which reduces the effect of temperature variation on pressure measurements. Cable 175 provides input power and also carries output signals to an electric control system for a therapeutic catheter or other such system.

Catheter 114 comprises a long, small-diameter hollow tube 120 having a distal end 122, a proximal end 124, and lumen 121 extending between the distal end 122 and proximal end 124. The proximal end 124 passes through luer lock connector 181 and housing 179 to attach to transducer 142 at tube adapter 147 with tube connector 128. Luer lock connector 181 is provided for connection to other apparatus, such as a therapeutic catheter having a mating Luer lock connector.

Distal end 122 of catheter 114 contains a thin-walled section 126 where the tube wall thickness is reduced. Tube 120 contains a first liquid 132, a second liquid 134, and a gel-like material 130. First liquid 132 is contained within proximal end 124 and is in fluid contact with pressure sensor 174 substantially filling transducer space 125. Gel-like material 130 is contained within distal end 122, but due to pressure and temperature fluctuations, may move slightly within distal end 122. Second liquid 134 fills the remaining space within hollow tube 120 and is in fluid communication with gel-like material 130 and first liquid 132. Thin-wall section 126 also provides the benefit of allowing an increased surface area of gel-like material 130 exposed to the body fluid while allowing the use of a thicker wall in all or some of the main portion of tube 120 in order to minimize compliance. This is especially relevant when the main portion of hollow tube 120 is constructed of a relatively compliant material such as a polymer. Thin-wall section 126 also provides a larger cross section of lumen 121 compared with proximal end 124. This reduces the movement of gel-like material 130 at distal end 122 caused by volumetric changes of first liquid 132 and second liquid 134.

First liquid 132 and second liquid 134 are low-viscosity, low-vapor-pressure liquids having a minimal compliance and are of a composition such that they are not soluble in each other. First liquid 132 is preferably non-corrosive, hydrophobic, and non-ionic since it may be in contact with the inner components of transducer 142. Further, first liquid 132 may be chosen to minimize leakage between sensor 174 and mount substrate 149.

In some embodiments, first liquid 132 will have the characteristic of being non-electrically conductive (i.e., non-polar and having high dielectric strength). A low-vapor-pressure liquid is desired to keep the amount of trapped air in the sensor to a minimum and to accommodate filling under vacuum. The low-vapor-pressure liquid is back-filled into transducer 142, after liquid space 125 has been evacuated. A low vapor pressure allows a higher vacuum to be applied to pressure transducer 142, thereby lowering the amount of trapped air. If a fluorinated hydrocarbon liquid is used as first liquid 132, most or all of the remaining air will be absorbed into the liquid, since it will absorb more air than most other liquids. This will result in removing most of the air bubbles. Lowering the amount of trapped air bubbles reduces the compliance of the system and as a result improves frequency response. In some embodiments, first liquid 132 is non-polar, not soluble in second liquid 134, and hydrophobic, therefore protecting the pressure transducer die from a potentially polar second liquid 134, both electrically and physically.

Second liquid 134 may or may not be electrically conductive. Second liquid 134 preferably has a low thermal coefficient of expansion, low viscosity, and low density. The low thermal coefficient of expansion property helps to reduce expansion/contraction due to temperature fluctuations, and therefore reduces the movement of gel-like material 130 at distal end 122. Reduction of movement of gel-like material 130 is important in order to avoid the formation of a void in gel-like material 130 at distal end 122 which may promote the formation of thrombus during use and therefore result in loss of performance. Second liquid 134 should also be insoluble to gel-like material 130. Low viscosity and low density liquids enable catheter 114 to have a higher frequency response (i.e., bandwidth) due to the reduction of friction and momentum losses. The low density liquid also helps to minimize artifacts due to head pressure.

First liquid 132 and second liquid 134 may comprise, for example, water, saline, inert fluorinated hydrocarbon, silicon oils, alcohols, and water solutions such as propylene glycol dispersed in water. Both liquids 132 and 134 must be non-toxic (in case of leakage). First liquid 132 may have a higher coefficient of thermal expansion than second liquid 134. In addition, first liquid 132 should have a low vapor pressure, low viscosity, and be non-corrosive. Since tube 120 contains substantially more second liquid 134, the two-liquid system overall will have a lower coefficient of expansion and a higher frequency response. This also greatly reduces the amount of movement of the gel-like material 130 due to thermal expansion/contraction of the liquids, resulting in improved patency. The use of two liquids also allows the use of a longer and smaller diameter tube 120 while maintaining a high frequency response and minimizing movement of gel-like material 130.

Gel-like material 130 is a relatively viscous and hydrophobic liquid/solid material. In one embodiment, gel-like material 130 is cross-linked and has a surface energy which increases its tendency to adhere to the inside walls of distal end 122. Any non-toxic and minimally thrombogenic material capable of flowing as does a viscous liquid and exhibiting intramolecular forces which makes it less likely to migrate or be dislodged from distal end 122 is acceptable. Additionally, the gel-like material 130 may contain an anti-thrombogenic substance to prevent clot formation, such as, for example, heparin and warfarin.

In some embodiments, tube 120 can be made from any biocompatible material. Tube 120 may have an outside diameter of 0.5 mm and an inside diameter of 0.2 mm. The length of tube 120 depends on the particular use involved, but can range from about 5 mm to 4 meters. Tube 120 can be made from any number of materials that provide the general characteristics of pushability, flexibility, low compliance, biocompatibility, abrasion resistance, ability to contain first liquid 132 and second liquid 134, and in some embodiments, be electrically conductive. Relative stiffness of tube 120 will depend on the application. Tube 120 may be very stiff for use where a stiff probe is required, or relatively flexible when used, for example, within narrow vasculature or within the lumen of a therapeutic/diagnostic catheter. Materials for tube 120 may include 316 stainless steel, Nitinol, titanium, MP52, MP35N, polyamide, polyimide, impregnated plastic, polytetra fluoroethylene, polyethylene, polyurethane, polyvinyl chloride, or polypropylene.

Tube 120, when made from most metals, will have a very low compliance compared with a tube made from polymer materials. The use of metals, in turn, increases the frequency response of catheter 114. A metal tube 120 will also withstand higher torsional and longitudinal stress/strain. The use of metal further provides the benefit of a longer and smaller diameter tube 120 while maintaining good frequency response, due to the low compliance of the material.

In another embodiment, an antithrombotic coating is applied to pressure transmission catheter 120. This antithrombotic coating may contain, for example, heparin, and be attached to tube 120 using, for example, the Photolink® process (Surmodics, Eden Prairie, Minn.). This will increase the hemocompatibility of the system. Similarly, a lubricious coating (for example, Parylene C® by Union Carbide) may be applied to catheter 120 to reduce friction when sliding catheter 120 into the lumen of a therapeutic/diagnostic catheter. In another embodiment, distal end 122 may further comprise a noble metal (such as platinum-iridium) sleeve, ring, or coating. Such a material is known to be antithrombogenic and also radio-opaque. Radio-opacity may be a benefit while placing the catheter.

A removable cover 141 is provided to protect distal end 122 when packaged and prior to use. Gel-like material 130 is typically rather tacky and would get dirty if not protected. Cover 141 is removed just prior to catheter use. In one embodiment, removable cover 141 is comprised of silicone tubing that is removed by grasping and pulling off distal end 122. In another embodiment, cover 141 is comprised of a peel-away cover that can be separated into pieces longitudinally to facilitate removal.

FIG. 2 shows a side view in partial cross-section illustrating generally, by way of example, but not by way of limitation, one embodiment of portions of a pressure sensing catheter 210. This embodiment is similar to the embodiment shown in FIG. 1. For convenience, similar components are not described here. In this embodiment, hollow tube 220 comprises a metal material. Therefore, tube 220 contains liquid 234 which is in fluid contact with pressure sensor 274 and gel-like material 230.

Liquid 234 has a low thermal coefficient of expansion, low viscosity, low density, and minimal compliance. Liquid 234 is preferably non-corrosive, and non-ionic since it may be in contact with metallic components of transducer 242. Further, liquid 234 may be chosen to minimize leakage through the joint between transducer 242 and mount substrate 249. Liquid 234 may comprise, for example, water, saline, inert fluorinated hydrocarbon, silicon oils, alcohols, and water solutions such as propylene glycol dispersed in water. Liquid 234 should be non-toxic (in case of leakage) and also be insoluble to gel-like material 230.

FIG. 3 shows a side view in partial cross-section illustrating generally, by way of example, but not by way of limitation, one embodiment of portions of a pressure and electrical signal sensing catheter 310. This embodiment is similar to the embodiment shown in FIG. 1. For convenience, similar components are not described here.

In this embodiment, hollow tube 320 comprises an electrically conductive material. Further, catheter 310 includes electrical connections 378 coupled to proximal end 324 of hollow tube 320. Hollow tube 320 is also coated with electrical insulation layer 338. Since hollow tube 320 is electrically conductive, it may be used as an electrode to sense and transmit an electric signal. It may be desired to restrict the electrical signal sensing portion of electrode 336 to distal end 322. Electric insulation layer 338 covers substantially the entire length of tube 320 except for a portion of tube 320 at distal end 322 or other portion of interest. This portion is identified as electrode 336. Electrode 336 senses an electrical signal which is electrically transmitted along tube 320 to electric insulation layer 378. Layer 338 may be a coating, a film, or a tube-like component and may be comprised of, for example, Parylene, silicon nitride, silicon oxide, or Teflon.

External connection 383 is provided as an attachment site for external devices, such as, for example, an indifferent electrode. External connection 383 is connected to temperature compensation electronics 377 through electrical connection 344. Electrical signals are then able to be communicated to outside devices though cable 375.

FIG. 4 shows a side view in partial cross-section illustrating generally, by way of example, but not by way of limitation, one embodiment of portions of a pressure and electrical signal sensing catheter 410. This embodiment is similar to the embodiment shown in FIG. 3. For convenience, similar components are not described here. In this embodiment, hollow tube 420 comprises a metal material.

Therefore, tube 420 contains liquid 434 which is in fluid contact with pressure sensor 474 and gel-like material 430.

Liquid 434 will have the characteristic of being non-electrically conductive (i.e., non-polar and having high dielectric strength). Additionally, liquid 434 should have a low thermal coefficient of expansion, low viscosity, low density, and minimal compliance. Liquid 434 is preferably non-corrosive, hydrophobic, and non-ionic since it may be in contact with metallic components of transducer 442. Further, liquid 434 may be chosen to minimize leakage through the joint between transducer 442 and mount substrate 449. Liquid 434 may comprise, for example, water, saline, inert fluorinated hydrocarbon, silicon oils, alcohols, and water solutions such as propylene glycol dispersed in water. Liquid 434 should be non-toxic (in case of leakage), and also be insoluble to gel-like material 430.

FIG. 5 shows a side view in partial cross-section illustrating generally, by way of example, but not by way of limitation, one embodiment of portions of a pressure and electrical sensing catheter 510. Catheter with physiological sensor 510 is comprised generally of a pressure transducer/electronics assembly 573 and pressure and electric signal transmission catheter 514. Assembly 573 comprises pressure transducer 542, electronics 577, including temperature compensation circuitry which compensates for variations in ambient temperature, and appropriate electrical connections 544, all housed in main housing 579. Assembly 573 terminates with electrical cable 575 which provides input power and also carries output signals to an electric control system for a therapeutic catheter or other such systems. Catheter 514 comprises a small diameter hollow tube 520 having a distal end 522 and a proximal end 524. The proximal end 524 enters assembly 573 through Luer lock 581. Hollow tube 520 is comprised of an electrically non-conductive material, such as, for example, polyethylene. The electrical characteristics of this embodiment are accomplished by embedding a conductor within hollow tube 520, such as shown in FIG. 6, for example.

FIG. 6 shows a side view in partial cross-section illustrating generally, by way of example, but not by way of limitation, one embodiment of the distal portion of the catheter with physiological sensor 510 (as shown in FIG. 5). In this embodiment, hollow tube 520 comprises an electrically non-conductive material, and further includes an electrically conductive distal end 522, filar coil 645, electrical connection 639, and tube joint 637. Coil 645 is embedded in tube 520 and runs substantially the entire length of tube 520. At distal end 522, coil 645 terminates at connection 639 and is in electrical communication with electrode 635. At proximal end 524 (as shown in FIG. 5), coil 645 connects with sensor electrical connection 543. Electrode 635 is a separate electrically conductive tube that is attached to distal end 522 by a joint 637. The electrode 635 senses an electrical signal which is electrically transmitted along filar coil 645 to connection 543 (as shown in FIG. 5). In other embodiments, electrode 635 may be an integral part of tube 520, such as, for example, by dispersion of an electrically conductive material molded into tube 520, and by a deposited layer of electrically conductive material. In other embodiments, coil 645 may, for example, be a slender wire that is embedded in, lying outside, or lying inside tube 520. Other methods to electrically communicate an electric signal from electrode 635 to connection 543, may, for example, include depositing an electrically conductive material as a strip to the outside of tube 520 and as a dispersion of electrically conductive material molded along length of tube 520.

The catheter with physiological sensor may be made from certain materials or used in certain circumstances that require the distal end of the catheter to be made more rugged than that provided by an unmodified hollow tube distal portion, with or without a thin-wall section. A ruggedized feature may be required to resist distal end kinking or collapse. FIG. 7 illustrates generally, by way of example, but not by way of limitation, one embodiment of distal end 722 of a catheter showing ruggedizing feature 790. Distal end 722 can be used with the various catheter embodiments shown and described herein. Ruggedizing feature 790 can be attached to distal end 722, over which a compliant membrane 789 is placed. In another embodiment, ruggedizing feature 790 may be slid over thin wall section 726 to add support to distal end 722, in which case compliant membrane 789 is not needed. In another embodiment, ruggedizing feature 790 is created directly from hollow tube 720 by laser cutting, photo etching, other etching process, molding, or by machining, leaving a mesh-like pattern. Compliant membrane 789 is then placed on the ruggedized feature, for example, by sputtering, vapor deposition over a mandrel temporally placed in the lumen, dipping, casting over molding, or by sliding over a compliant tube, such as heat shrink tubing. In another embodiment, the fabrication process does not cut completely through thin wall section 726 but leaves thin compliant areas surrounded by areas of thicker, more rigid material.

Ruggedizing feature 790 comprises a support structure made from a relatively rigid material as compared with thin wall section 726. Ruggedizing feature 790 provides a distal tip 722 that is more resistant to kinking and collapse, while allowing the compliant portion spanning the spaces within ruggedized feature 790 of thin wall section 726 to respond to pressure, transmitting the pressure to second liquid 734 and to gel-like material 730.

In another embodiment, tube 720 is fabricated of a polymer, such as, for example, a 60 D hardness urethane that is very flexible. In this embodiment, ruggedizing feature 790 may be fabricated from a much harder polymer or from metal.

Figure 8:
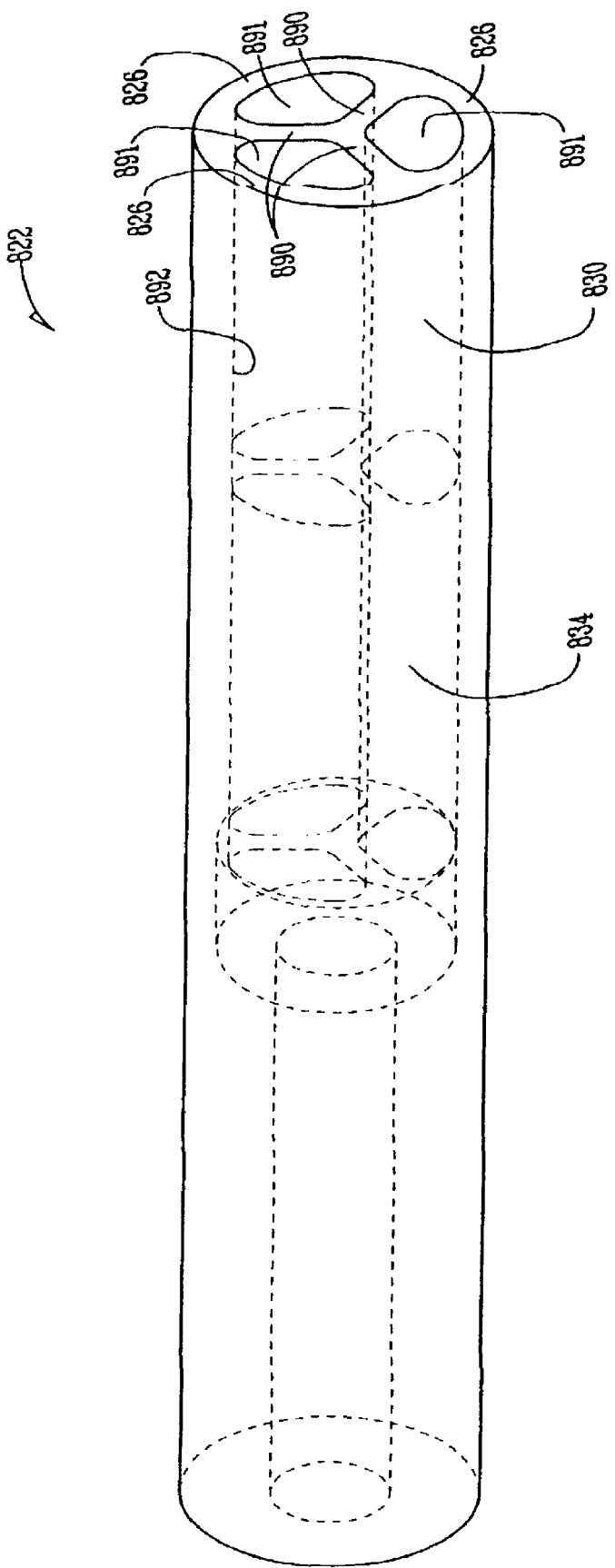
FIG. 8 is a partial cross-sectional side view of an embodiment of a distal end of a catheter with a physiological sensor.

FIG. 8 illustrates generally, by way of example, but not by way of limitation, one embodiment of distal end 822 of a catheter showing ruggedizing feature 892. Distal end 822 can be used with the various catheter embodiments shown and described herein. Distal end 822 is comprised of multiple lumens 891. The inner portion of these structures is formed by ribs 890 which act to increase resistance to collapse and kinking of distal end 826. Thin wall sections 822 are compliant and transfer the outside pressure to second liquid 834 and gel-like material 830 contained within the lumens 891. In some embodiments, the distal 2–4 mm of feature 892 is filled with gel-like material 830, while the remaining portion is filled with second liquid 834.

FIG. 9 illustrates generally, by way of example, but not by way of limitation, one embodiment of distal end 922 of the pressure transmission catheter showing ruggedizing feature 992. A stent-like insert 993 is placed within relatively compliant thin wall section 926, to provide a reinforcing structure that provides resistance to kinking and collapse of distal end 922. Stent 993 may be fabricated from a metal tube (for example, nickel titanium alloy (Nitinol), titanium, 316 stainless steel, or platinum) that is, for example, laser cut, etched, or machined to form openings through which thin wall section 926 is directly exposed to second liquid 934 and gel-like material 930. Stent 993 may alternately be formed, for example, from a wire, a plastic, polymer (for example, acetal resin, polytetra fluorethane, polyethylene, polyurethane, polypropylene, polyamide, polyimide, or acetyl butadiene styrene) and other relatively rigid materials. Stent openings 994 are sized appropriately such that thin wall section 926 can efficiently transfer the dynamic components of the pressure signal into second liquid 934 and gel-like material 930 in order to obtain a high-fidelity reproduction of the desired pressure signal. In other embodiments, stent 993 is placed on the outside of thin wall section 926. In other embodiments, stent 993 is molded directly into the distal end.

It may be desired to use the catheter with physiological sensor as a guidewire. It may also be desired to use the catheter with physiological sensor as a stand-alone diagnostic catheter; that is, used without first placing a therapeutic catheter within the vasculature. For these uses, the catheter with physiological sensor must be able to traverse narrow, tortuous vasculature (such as coronary arteries). Because of this, it may be desired that the catheter distal tip be very flexible and resilient to kinking, as well as non-injurious to the vasculature. FIG. 10 illustrates generally, by way of example, but not by way of limitation, one embodiment of distal end 1022 of the pressure transmission catheter showing flexible tip feature 1088. In one embodiment, flexible tip feature 1088 consists of a spring-like feature 1097 tenninating in a smooth head 1098. The spring-like feature 1097 is attached to distal end 1022, for example, by wrapping over, sliding inside, and/or molded into distal end 1022. In one embodiment, flexible tip feature 1088 is up to 3 cm long.

FIG. 11 illustrates generally, by way of example, but not by way of limitation, one embodiment of distal end 1122 of the pressure transmission catheter showing flexible tip feature 1188. Flexible tip feature 1188 comprises a spring-like feature 1197, a smooth head 1198, and a cone-shaped insert 1195. Cone-shaped insert 1195 is perforated with numerous holes 1196 to allow gel-like material 1130 movement and to allow gel-like material 1130 to be exposed to the pressure environment. The cone-shaped insert 1195 is inserted into distal end 1122.

FIG. 12 illustrates generally, by way of example, but not by way of limitation, one embodiment of distal end 1222 of pressure transmission catheter showing flexible tip feature 1288. This embodiment is similar to the embodiment shown in FIG. 10. For convenience, similar components are not described here. In this embodiment, thin-wall section 1226 has the addition of numerous slits 1299 in the portion that is filled with gel-like material 1230. The addition of slits 1299 is to allow more of the gel-like material 1230 to respond to the pressure environment, and to allow the tip to be more flexible.

FIG. 13 shows a side view in partial cross-section illustrating generally, by way of example, but not by way of limitation, and an environment in which it is used, one embodiment of portions of a catheter with physiological sensor 1310 which comprises generally a pressure transducer/electronics assembly 1373 and pressure transmission catheter 1314. Pressure transmission catheter 1314 is shown as used with a therapeutic/diagnostic catheter 1350. Transmission catheter 1314 is inserted into lumen 1356 of therapeutic/diagnostic catheter 1350. This is done by inserting distal end 1322 of pressure transmission catheter 1314 into lumen 1356 and slidably moving through lumen 1356 until distal end 1322 projects beyond distal end 1351 of the therapeutic/diagnostic catheter.

In one embodiment, the therapeutic/diagnostic catheter 1350 includes an electrode 1372 with connection 1376 to external connection 1383. Electrode 1372 is attached or made part of catheter 1350 such that when catheter 1350 is in use, electrode 1372 can be used to sense a reference physiological, electrical signal needed for particular therapies and diagnoses. In this embodiment, the signal from reference electrode 1372 is compared with the signal from the catheter electrode. Providing reference electrode 1372 on catheter 1350 negates the need for the use of extemal electrodes to measure, for example, an electrocardiogram (ECG) that are prone to inaccurate measurement, noise, and disconnection. Reference electrode 1372 may be provided on catheter 1350, for example, by attachment, as a molded in place part or feature, or as a deposition or coating.

Figure 14:
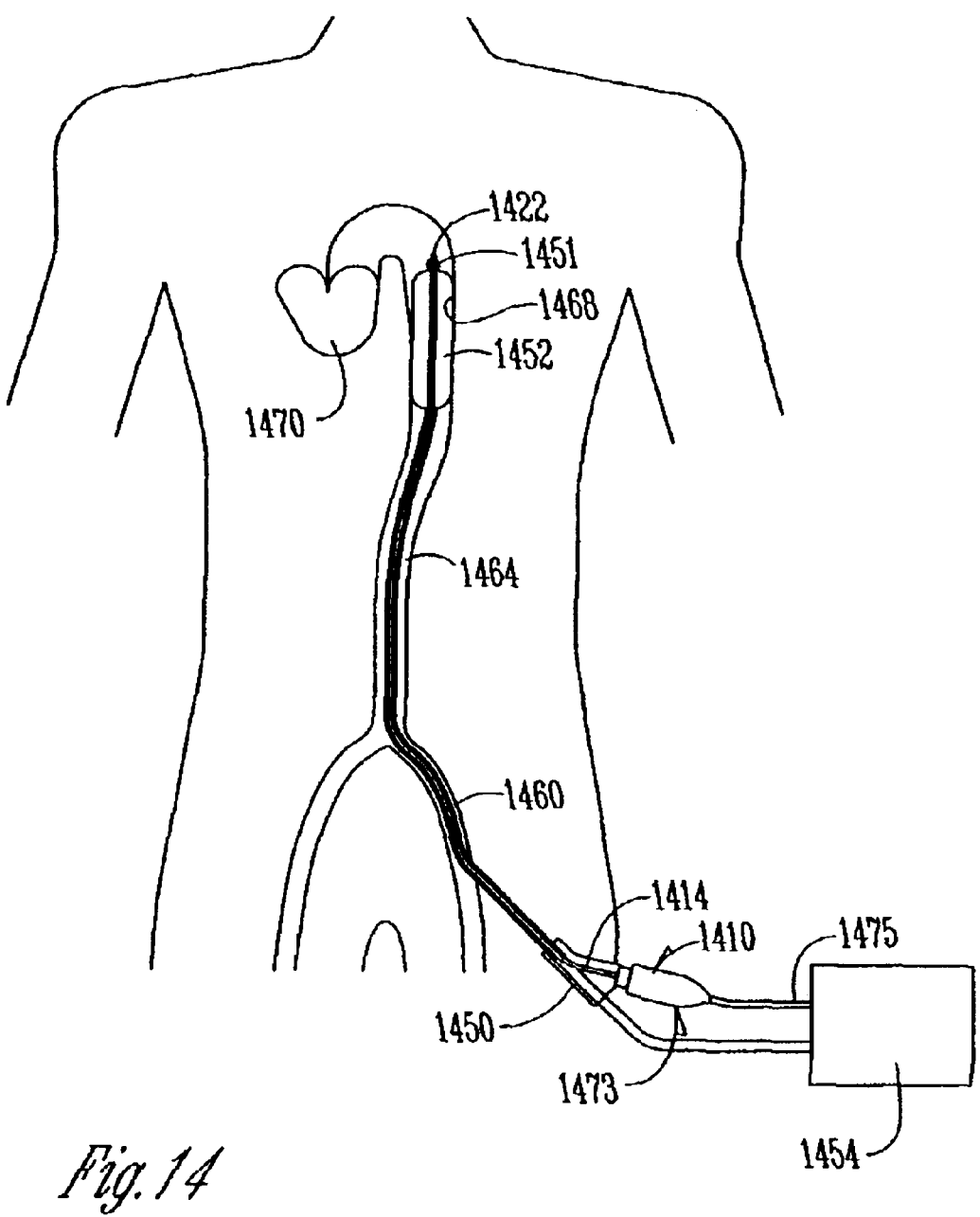
FIG. 14 is a representation showing an embodiment of a pressure and electric signal sensing catheter threaded through an intra-aortic balloon catheter lumen, the balloon catheter having first been inserted into the femoral artery and advanced up to the descending aorta.

FIG. 14 illustrates generally, by way of example, but not by way of limitation, and an environment in which it is used, one embodiment of potions of a pressure and electrical sensing catheter 1410 with a typical therapeutic catheter 1450, in this case an intra-aortic balloon catheter (e.g., Profile® 8 FR. Intra-Aortic Balloon (IAB) Catheter, Data-scope Corporation, Fairfield, N.J.). An opening is typically made in one of the femoral arteries 1460 into which is inserted a guidewire (not shown), which is long, thin, and flexible. The guidewire is threaded up through the abdominal aorta 1464 to the descending thoracic aorta 1468. Once the guidewire is correctly placed within the vasculature, therapeutic catheter 1450 is threaded over a guidewire (not shown) and advanced to the treatment site. The guidewire is then removed. Pressure transmission catheter 1414 is advanced through a lumen of catheter 1450 until distal end 1422 projects beyond distal end 1451 of catheter 1450. This allows the pressure and electrical measurements to be taken on the upstream (high pressure) side of intra-aortic balloon catheter balloon 1452. The pressure transmission catheter 1414 terminates at the pressure transducer/electronics assembly 1473 which is connected through cable 1475 to the intra-aortic balloon catheter control system 1454. The intra-aortic balloon catheter 1450 terminates at control system 1454. Catheter electrode 1436 senses an electric signal from the heart 1470, e.g., an electrocardiogram signal, which is used by control system 1454 to trigger inflation and deflation of balloon 1452. Balloon 1452, when inflated, displaces blood in the artery. If timed correctly, this results in an increase in systolic pressure and increased perfusion of the coronary arteries (not shown). The pressure measurements are used to calibrate control system 1454 to take into account the time lag between the electrical impulse from the heart 1470 and cardiovascular response.

Some disclosed embodiments of the catheter with physiological sensor provide a prefilled catheter-based pressure sensing system that can traverse a lumen of a diagnostic/therapeutic catheter. Previous pressure sensing catheters, especially those used with intra-aortic balloons, are not suitable because they are either too large, too compliant to provide accurate pressure measurements, too expensive, too inconvenient to use, and/or have other limitations, particularly those associated with being non-prefilled. Prefilling provides the added assurance of high quality control, reduced preparation time prior to use, and greatly reduced likelihood of air bubbles in the lumen. Additionally, a less complex and more accurate and reliable system for detecting electrical signals is provided for treatments requiring the detection of such signals.

Existing devices gather control data using separate electrodes. These electrodes sense an electric signal to control therapeutic catheters, such as the inflation/deflation of an intra-aortic balloon catheter. These separate electrodes are prone to electrical interference, are not precise in electrical detection, and are prone to environmental affects and accidental disconnection. These separate electrodes typically must be placed away from the target site, and therefore do not precisely measure the desired signals. Some embodiments of the disclosed pressure and electrical sensing catheter provide the ability to gather pressure measurements beyond the intra-aortic balloon catheter balloon location during the entire treatment period as well as providing electrical signals to the balloon control system, making separate electrodes unnecessary. Since the catheter electrode is placed at the target site, the desired electrical signal is measured, minimizing multiple signals and electrical noise associated with surface skin electrodes. In some embodiments, the catheter electrode is also an integral part of the catheter and therefore cannot be accidentally disconnected.

The disclosed embodiments provide an apparatus that obtains blood pressure measurements that are reliable and of high quality. Such an improved catheter capable of providing reliable high-fidelity blood pressure signals could also open up the possibility of implementing closed loop control, eliminating the need for manual adjustments of the timing of balloon inflation based on observation of the measured blood pressure waveform. Some embodiments of the pressure sensing catheter embodied here are also useful as diagnostic catheters for measurement of left ventricular pressure of the heart. For example, a guiding catheter containing a lumen of sufficient size to accommodate the disclosed pressure sensing catheter could be directed transvascularly into the left ventricle. The guiding catheter could be any of a series of standard catheters that are currently used for crossing the aortic valve retrograde into the left ventricle.

In another embodiment, the distal tip of the catheter with physiological sensor incorporates a flexible tip to allow the catheter to be guided into narrow, tortuous vasculature, such as coronary arteries, with or without a guiding catheter. This would allow the catheter to assess stenosis severity by measuring fractional flow reserve.

In some embodiments, the catheter with physiological sensor has an advantageously very low compliance. The catheter can be fabricated with a compliant thin wall distal end, and all or most of the thin-wall distal end can be exposed to the body fluid. By using a compliant material on the distal end, the pressure signal can be transmitted through the compliant material into the catheter lumen and transmitted by the catheter liquid. In embodiments where the pressure transducer and main portion of the catheter have a significant compliance, the thin wall compliant distal end design results in better frequency response than can be achieved if the pressure signal were transmitted to the lower-viscosity catheter liquid through only the viscous gel-like material.

In some embodiments, the catheter with physiological sensor may be used such that pressure measurements may be taken beyond the therapeutic/diagnostic catheter lumen tip as well as at some point between the distal and proximal ends of the catheter. For example, an opening in the therapeutic/diagnostic catheter could be made at a point along its length through which pressure measurements may be taken.

CONCLUSION

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A catheter, comprising:
   a pressure transducer that provides a signal which varies as a function of pressure;
   a hollow tube having a distal end, a proximal end, and a lumen extending between the proximal end and the distal end, the pressure transducer coupled to the proximal end;
   a gel-like material positioned in the lumen at the distal end;
   at least one liquid which fills the lumen and is in communication with the pressure transducer and the gel-like material; and
   a ruggedized tip disposed at the distal end of the hollow tube.

2. The catheter according to claim 1, wherein the hollow tube comprises a material selected from the group consisting of polyamide, polyimide, impregnated plastic, polytetra fluorethylene, polyethylene, polyurethane, polyvinyl chloride, and polypropylene.

3. The catheter according to claim 1, wherein the hollow tube comprises a metal selected from the group consisting of 316 stainless steel, Nitinol, titanium, MP35N, and MP52.

4. The catheter according to claim 1, wherein the distal end further comprises a thin-wall portion.

5. The catheter according to claim 1, wherein the at least one liquid is selected from the group consisting of water, saline, fluorinated hydrocarbon, silicone oils, alcohols, and propylene glycol dispersed in water.

6. The catheter according to claim 1, wherein the gel-like material comprises a non-toxic and minimally thrombogenic material.

7. The catheter according to claim 1, wherein the gel-like material further comprises an anti-thrombogenic substance selected from the group consisting of heparin and warfarin.

8. The catheter according to claim 1, wherein at least a portion of the hollow tube is electrically conductive.

9. The catheter according to claim 8, wherein the hollow tube is substantially covered with an insulating material.

10. The catheter according to claim 1, wherein the distal end includes an electrically conductive portion which acts as an electrode for detecting an electric signal.

11. The catheter according to claim 10, and further including a conductor that is coupled to the electrically conductive portion and disposed along the length of the hollow tube.

12. The catheter according to claim 1, wherein the ruggedized tip comprises ribs dividing the lumen into a plurality of lumens at the distal end.

13. The catheter according to claim 1, wherein the ruggedized tip comprises a stent inserted into the lumen at the distal end of the hollow tube.

14. The catheter according to claim 13, wherein the stent comprises a braided wire tube.

15. The catheter according to claim 13, wherein the stent comprises an expanded metal mesh tube.

16. The catheter according to claim 1, wherein the distal end further comprises a plurality of semi-circumferential elongated holes.

17. The catheter according to claim 1, wherein the ruggedized tip comprises:
a mesh-like feature formed in the distal end of the hollow tube; and
a compliant membrane disposed over the outer surface of the mesh-like feature.

18. A guidewire catheter, comprising:
a pressure transducer that provides a signal which varies as a function of pressure;
a hollow tube having a distal end, a proximal end, and a lumen extending between the proximal end and the distal end, the pressure transducer coupled to the proximal end;
a gel-like material positioned in the lumen at the distal end;
at least one liquid which fills the lumen and is in communication with the pressure transducer and the gel-like material; and
a flexible tip disposed at the distal end of the hollow tube.

19. The catheter according to claim 18, wherein the hollow tube comprises a material selected from the group consisting of polyamide, polyimide, impregnated plastic, polytetra fluorethylene, polyethylene, polyurethane, polyvinyl chloride, and polypropylene.

20. The catheter according to claim 18, wherein the hollow tube comprises a metal selected from the group consisting of 316 stainless steel, Nitinol, titanium, MP35N, and MP52.

21. The catheter according to claim 18, wherein the distal end further comprises a thin-wall portion.

22. The catheter according to claim 18, wherein the at least one liquid is selected from the group consisting of water, saline, fluorinated hydrocarbon, silicone oils, alcohols, and propylene glycol dispersed in water.

23. The catheter according to claim 18, wherein the gel-like material comprises a non-toxic and minimally thrombogenic material.

24. The catheter according to claim 18, wherein the gel-like material further comprises an anti-thrombogenie substance selected from the group consisting of heparin and warfarin.

25. The catheter according to claim 18, wherein at least a portion of the hollow tube is electrically conductive.

26. The catheter according to claim 25, wherein the hollow tube is substantially covered with an insulating material.

27. The catheter according to claim 18, wherein the distal end includes an electrically conductive portion which acts as an electrode for detecting an electric signal.

28. The catheter according to claim 27, and further including a conductor that is coupled to the electrically conductive portion and disposed along the length of the hollow tube.

29. The catheter according to claim 18, wherein the distal end further comprises a plurality of semi-circumferential elongated holes.

30. The catheter according to claim 18, wherein the flexible tip comprises:
a coil having a first end and a second end; and
a rounded head,
wherein the rounded head is coupled to the first end of the coil, and the second end of the coil is coupled to the distal end of the hollow tube.

31. The catheter according to claim 18, wherein the flexible tip comprises:
a coil having a first end and a second end;
a rounded head;
a cone-shaped insert having a plurality of holes; and
wherein the rounded head is attached to the first end of the coil, and the second end of the coil is attached to the cone-shaped insert and wherein the cone-shaped insert is inserted into the distal end of the hollow tube.

32. A catheter, comprising:
a pressure transducer that provides a signal which varies as a function of pressure;
a hollow tube having a distal end, a proximal end, and a lumen extending between the proximal end and the distal end, the pressure transducer coupled to the proximal end;
a gel-like material positioned in the lumen at the distal end;
at least two liquids disposed within the hollow tube to provide a pressure communication link between the gel-like material and the pressure transducer.

33. The catheter according to claim 32, wherein the at least two liquids comprise:
a first liquid in communication with the pressure transducer; and a second liquid which substantially fills the lumen and is in communication with the gel-like material and the first liquid, and wherein the first liquid and the second liquid are not soluble with each other.

34. The catheter according to claim 32, wherein the hollow tube comprises a material selected from the group consisting of polyamide, polyimide, impregnated plastic, polytetra fluorethylene, polyethylene, polyurethane, polyvinyl chloride, and polypropylene.

35. The catheter according to claim 32, wherein the hollow tube comprises a metal selected from the group consisting of 316 stainless steel, Nitinol, titanium, MP35N, and MP52.

36. The catheter according to claim 32, wherein the distal end further comprises a thin-wall portion.

37. The catheter according to claim 32, wherein the at least two liquids are selected from the group consisting of water, saline, fluorinated hydrocarbon, silicone oils, alcohols, and propylene glycol dispersed in water.

38. The catheter according to claim 32, wherein the gel-like material comprises a non-toxic and minimally thrombogenic material.

39. The catheter according to claim 32, wherein the gel-like material further comprises an anti-thrombogenic substance selected from the group consisting of heparin and warfarin.

40. The catheter according to claim 32, wherein at least a portion of the hollow tube is electrically conductive.

41. The catheter according to claim 40, wherein the hollow tube is substantially covered with an insulating material.

42. The catheter according to claim 32, wherein the distal end includes an electrically conductive portion which acts as an electrode for detecting an electric signal.

43. The catheter according to claim 42, and further including a conductor that is coupled to the electrically conductive portion and disposed along the length of the hollow tube.

44. The catheter according to claim 32, and further including a ruggedized tip including ribs separating the lumen into a plurality of lumens at the distal end.

45. The catheter according to claim 32, wherein the distal end further comprises a stent inserted into the lumen of the distal end of the hollow tube.

46. The catheter according to claim 45, wherein the stent comprises a braided wire tube.

47. The catheter according to claim 45, wherein the stent comprises an expanded metal mesh tube.

48. The catheter according to claim 32, wherein the distal end further comprises a plurality of semi-circumferential elongated holes.

49. The catheter according to claim 32, and further comprising a flexible tip comprising:
    a coil having a first end and a second end;
    a rounded head; and
    wherein the rounded head is coupled to the first end of the coil, and the second end of the coil is coupled to the distal end of the hollow tube.

50. The catheter according to claim 32, and further comprising a flexible tip comprising:
    a coil having a first end and a second end;
    a rounded head;
    a cone-shaped inset having a plurality of holes; and
    wherein the rounded head is attached to the first end of the coil, and the second end of the coil is attached to the cone-shaped insert and wherein the cone-shaped insert is inserted into the distal end of the hollow tube.

51. A system, comprising:
    a sensing catheter that includes a sensor for sensing a physiological parameter;
    the sensing catheter including an electrical output signal related to the sensed physiological parameter;
    a control system coupled to the electrical output signal of the sensing catheter;
    a therapeutic catheter includinig at least one input that receives an input from the control system based on the output signal of the sensing catheter; and
    wherein the therapeutic catheter includes a hollow tube having a lumen for receiving the sensing catheter and placing the sensor of the sensing catheter in a position to sense the physiological parameter.

52. The system of claim 51, wherein the therapeutic catheter comprises an intra-aortic balloon catheter having a balloon and wherein the control system provides a feed-back control loop that controls the inflation/deflation of the balloon based on signals from the sensing catheter.

53. The system of claim 52, wherein the signals from the sensing catheter include a pressure signal.

54. The system of claim 52, wherein the signals from the sensing catheter include an electrocardiogram (ECG) signal.

55. The system of claim 51, wherein the sensing catheter includes:
    a pressure transducer that provides a signal which varies as a function of pressure;
    a hollow tube having a distal end, a proximal end, and a lumen extending between the proximal end and the distal end, the proximal end in communication with the pressure transducer;
    a gel-like material positioned in the lumen at the distal end; and
    at least one liquid which fills the lumen and is in communication with the pressure transducer and the gel-like material.

56. The system of claim 51, wherein the therapeutic catheter further includes a reference electrode coupled to an exterior of the hollow tube of the therapeutic catheter.

57. A catheter, comprising:
    a pressure transducer that provides a signal which varies as a function of pressure;
    a hollow, metal tube having a distal end, a proximal end, and a lumen extending between the proximal end and the distal end, wherein the hollow, metal tube comprises a metal selected from the group consisting of 316 stainless steel, Nitinol, titanium, MP35N, and MP52, the pressure transducer coupled to the proximal end;
    a gel-like material positioned in the lumen at the distal end; and
    at least one liquid which fills the lumen and is in communication with the pressure transducer and the gel-like material.

58. A catheter, comprising:
    a pressure transducer that provides a signal which varies as a function of pressure;
    a hollow, metal tube having a distal end, a proximal end, and a lumen extending between the proximal end and the distal end, the pressure transducer coupled to the proximal end;
    a gel-like material positioned in the lumen at the distal end; and
    at least one liquid which fills the lumen and is in communication with the pressure transducer and the gel-like material, wherein the at least one liquid is selected from the group consisting of water, saline, silicone oils, alcohols, and propylene glycol dispersed in water.

59. A catheter, comprising:

a pressure transducer that provides a signal which varies as a function of pressure;

a hollow, metal tube having a distal end, a proximal end, and a lumen extending between the proximal end and the distal end, the pressure transducer coupled to the proximal end;

a gel-like material positioned in the lumen at the distal end, wherein the gel-like material comprises a non-toxic and minimally thrombogenic material; and at least one liquid which fills the lumen and is in communication with the pressure transducer and the gel-like material.

60. A catheter, comprising:

a pressure transducer that provides a signal which varies as a function of pressure;

a hollow, metal tube having a distal end, a proximal end, and a lumen extending between the proximal end and the distal end, the pressure transducer coupled to the proximal end;

a gel-like material positioned in the lumen at the distal end, wherein the gel-like material further comprises an anti-thrombogenic substance selected from the group consisting of heparin and warfarin; and at least one liquid which fills the lumen and is in communication with the pressure transducer and the gel-like material.

61. A catheter, comprising:

a pressure transducer that provides a signal which varies as a function of pressure;

a hollow, metal tube having a distal end, a proximal end, and a lumen extending between the proximal end and the distal end, wherein the hollow tube is substantially covered with an insulating material, the pressure transducer coupled to the proximal end;

a gel-like material positioned in the lumen at the distal end; and at least one liquid which fills the lumen and is in communication with the pressure transducer and the gel-like material.

62. A catheter, comprising:

a pressure transducer that provides a signal which varies as a function of pressure;

a hollow tube having a distal end, a proximal end, and a lumen extending between the proximal end and the distal end, a portion of the distal end comprising at least one rib separating the lumen into a plurality of smaller lumens, the pressure transducer coupled to the proximal end;

a gel-like material positioned in the lumen at the distal end; and at least one liquid which fills the lumen and is in communication with the pressure transducer and the gel-like material.

63. A catheter, comprising:

a pressure transducer that provides a signal which varies as a function of pressure;

a hollow tube having a distal end, a proximal end, and a lumen extending between the proximal end and the distal end, the distal end, the pressure transducer coupled to the proximal end;

a gel-like material positioned in the lumen at the distal end;

a stent coupled to the distal end of the hollow tube; and at least one liquid which fills the lumen and is in communication with the pressure transducer and the gel-like material.

64. The catheter according to claim 63, wherein the stent coupled to the distal end of the hollow tube comprises a stent coupled to the lumen of the distal end of the hollow tube.

65. The catheter according to claim 63, wherein the stent coupled to the distal end of the hollow tube comprises the stent coupled to the outer surface of the distal end of the hollow tube.

66. The catheter according to claim 63, wherein the stent coupled to the distal end of the hollow tube comprises a stent imbedded into the distal end of the hollow tube.

67. The catheter according to claim 63, wherein the stenit comprises a braided wire tube.

68. The catheter according to claim 63, wherein the stent comprises an expanded metal mesh tube.

69. The catheter according to claim 63, wherein the stent comprises a perforated tube.

70. A catheter, comprising:

a pressure transducer that provides a signal which varies as a function of pressure;

a hollow tube having a distal end, a proximal end, and a lumen extending between the proximal end and the distal end, the hollow tube further comprises a plurality of holes proximate the distal end, the pressure transducer is coupled to the proximal end;

a gel-like material positioned in the lumen at the distal end and at the plurality of holes; and at least one liquid which fills the lumen and is in communication with the pressure transducer and the gel-like material.

71. The catheter according to claim 70, wherein the plurality of holes are of semi-circumferential elongated shape.

72. The catheter according to claim 70, wherein the plurality of holes form a mesh-like structure.

73. The catheter according to claim 70, further comprising a compliant membrane disposed over the plurality of holes.

74. A catheter, comprising:

a pressure transducer that provides a signal which varies as a function of pressure;

a hollow, metal tube having a distal end, a proximal end, and a lumen extending between the proximal end and the distal end;

a gel-like material positioned in the lumen at the distal end;

at least one liquid which fills the lumen and is in communication with the pressure transducer and the gel-like material; and a flexible tip comprising:
  a coil having a first end and a second end;
  a rounded head; and
  wherein the rounded head is coupled to the coil first end of the coil, and the second end of the coil is coupled to the distal end of the hollow tube.

75. A catheter, comprising:

a pressure transducer that provides a signal which varies as a function of pressure;

a hollow, metal tube having a distal end, a proximal end, and a lumen extending between the proximal end and the distal end;

a gel-like material positioned in the lumen at the distal end;
at least one liquid which fills the lumen and is in communication with the pressure transducer and the gel-like material; and
a flexible tip comprising:
 a coil having a first end and a second end;
 a rounded head;
 a cone-shaped insert having a plurality of holes; and
 wherein the rounded head is attached to the first end of the coil, and the second end of the coil is attached to the cone-shaped insert and wherein the cone-shaped insert is inserted into the distal end of the hollow tube.

* * * * *

UNITED STATES PATENT AND TRADEMARK OFFICE
CERTIFICATE OF CORRECTION

PATENT NO. : 6,296,615 B1 Page 1 of 1
DATED : October 2, 2001
INVENTOR(S) : Brockway et al.

It is certified that error appears in the above-identified patent and that said Letters Patent is hereby corrected as shown below:

Column 1,
Line 46, delete "inflation-deflation" and insert -- inflation/deflation --, therefor.

Column 2,
Line 44, delete "tun" and insert -- turn --, therefor.

Column 4,
Line 45, delete "luer" and insert -- Luer --, therefor.

Column 5,
Line 50, delete "ineit" and insert -- inert --, therefor.

Column 8,
Line 35, delete "ajoint" and insert -- a joint --, therefor.

Column 10,
Line 11, delete "FIG. 11 illustrates" and insert -- FIGS. 11A and 11B illustrate --, therefor.
Line 64, delete "potions" and insert -- portions --, therefor.

Signed and Sealed this

Fourth Day of June, 2002

*Attest:*

JAMES E. ROGAN
*Attesting Officer*     *Director of the United States Patent and Trademark Office*